US005403293A

United States Patent [19]

Grabenkort

[11] Patent Number: 5,403,293

[45] Date of Patent: Apr. 4, 1995

[54] MOLDED PARTIAL PRE-SLIT RESEAL

[75] Inventor: Richard W. Grabenkort, Barrington, Ill.

[73] Assignee: Abbott Laboratories, Abbott Park, Ill.

[21] Appl. No.: 176,052

[22] Filed: Jan. 3, 1994

[51] Int. Cl.[6] .............................................. A61M 37/00

[52] U.S. Cl. ..................................................... 604/256

[58] Field of Search ................ 604/284, 283, 240–249, 604/256, 167, 415, 411, 905

[56] References Cited

U.S. PATENT DOCUMENTS

| | | | |
|---|---|---|---|
| 3,171,412 | 3/1965 | Braun | 604/244 |
| 4,781,693 | 11/1988 | Martinez et al. | 604/244 |
| 4,781,702 | 11/1988 | Herrli | 604/284 |
| 5,071,404 | 12/1991 | Larkin et al. | 604/244 |
| 5,178,107 | 1/1993 | Lynn et al. | 604/244 |
| 5,199,948 | 4/1993 | McPhee | 604/411 |
| 5,251,873 | 10/1993 | Atkinson et al. | 604/905 |
| 5,254,097 | 10/1993 | Schock et al. | 604/284 |
| 5,290,241 | 3/1994 | Kraus et al. | 604/284 |
| 5,295,657 | 3/1994 | Atkinson | 604/905 |
| 5,295,658 | 3/1994 | Atkinson et al. | 604/905 |

*Primary Examiner*—John D. Yasko
*Assistant Examiner*—Manuel Mendez
*Attorney, Agent, or Firm*—A. Nicholas Trausch

[57] ABSTRACT

This invention pertains to a reseal member made of a resilient material used for sealing a fluid access port. The reseal member is inserted into the fluid access port and prevents fluids from passing therethrough. The reseal member is provided with a slit or recess, or both, that allows a user to exert-minimal force to insert a blunt cannula into the reseal member to create a passage to pass fluids through the reseal member. Upon withdrawal of the blunt cannula, the reseal forms a generally fluid-tight seal so that fluids cannot pass through the reseal.

10 Claims, 2 Drawing Sheets

MOLDED PARTIAL PRE-SLIT RESEAL

FIELD OF THE INVENTION

The present invention relates generally to a penetrable reseal member used for sealing a fluid access port of a solution container, and more particularly to a reseal member for use with a blunt cannula to be inserted therethrough.

BACKGROUND OF THE INVENTION

Reseal members are widely used in medical solution containers to initially seal the container and later to prevent leakage of fluid from a container during and after the insertion of a cannula or needle to create a passage so that fluids may be removed or added to the container.

Typically a reseal member includes a generally cylindrical, solid, rubber body. To add or remove fluids, the reseal member must be pierced by a sharp cannula or needle. Sharp cannulas or needles are required to penetrate the reseal member because the reseal member is thick and solid at the insertion point.

"Accidental needle stick" is a great concern with the use of this type of reseal member since a sharp cannula or needle is needed to pierce the solid, rubber body. To overcome this potential danger, sharp cannulas or needles are being replaced with blunt cannulas. However, a blunt cannula cannot be inserted into the traditional type of reseal member without application of undesirably high force, which creates other potential dangers. The present invention is intended to overcome these potential dangers as well as to present several significant advantages.

SUMMARY OF THE INVENTION

This invention pertains to a resilient reseal assembly used for sealing and resealing a fluid access port, particularly in a medical solution container.

A fluid access port generally includes a cylindrical, peripheral wall with open ends. The reseal member of this invention is positioned within the fluid access port and is fitted in fluid tight relationship with the wall. The reseal member has an end portion positioned generally at one of the open ends of the peripheral wall preferably the distal and furtherest from the solution container body so that the reseal member can be penetrated by a blunt cannula. Thus, fluids may be passed into or removed from the solution container.

More specifically this invention relates to a reseal assembly for penetration by an associated blunt cannula. The reseal assembly seals a fluid port defined by a generally cylindrical wall having an open proximal end and an open distal end. The reseal assembly includes a resilient body portion having a generally frustoconical shape including a top surface, a side surface tapering from a top end to a bottom end, and a bottom surface. The resilient body further has a hollowed core in the resilient body from the bottom surface. The hollowed core has a generally conical shape tapering to a hinged region near the top surface. The hollow core defines two body sections positioned adjacent each other and joined to each other by at least the hinged region. The side surface of the resilient body has an annular groove circumferentially surrounding the resilient body near the top end. The reseal assembly further includes a stiff annular collar having a first inner annular edge and a second inner annular edge. The first inner edge is positionable within the annular groove of the resilient body so as to hold the top end of the resilient body. The second inner edge is positioned around the outer surface of the proximal end of the cylindrical fluid port to secure the collar and resilient body relative to the fluid port.

This invention contemplates that a user may insert a blunt cannula through the novel reseal member of the present invention with minimal insertion force. This invention also contemplates that upon passage of a blunt cannula through the reseal member, the reseal member forms a fluid-tight seal around the cannula so as to prevent leakage of fluids therethrough. It is further contemplated that upon withdrawal of the blunt cannula, the reseal member reforms a generally fluid-tight seal (by virtue of its resilience) so fluids will not pass therethrough.

These and other objects, features, and advantages of this invention are evident from the following description of a preferred embodiment of this invention with reference to the accompanying drawings.

DETAILED DESCRIPTION OF THE PREFERRED EMBODIMENT

Figure 1:
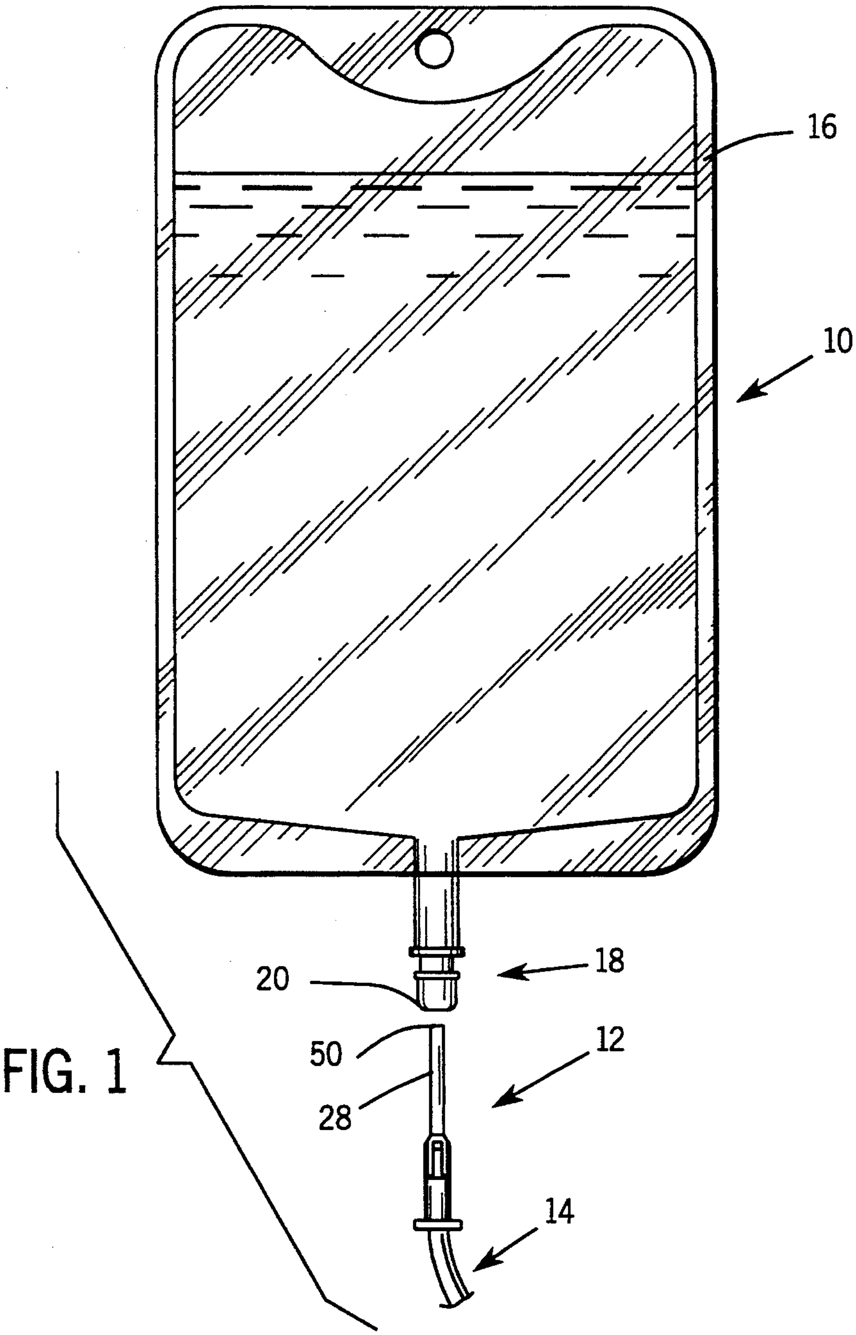
FIG. 1 is an elevational view of a solution container with a fluid port including a reseal member according to the present invention for use with the blunt entry device.

While the present invention is susceptible of embodiments in various forms, there is shown in the drawings and will hereinafter be described presently preferred embodiments, with the understanding that the present disclosure is to be considered as an exemplification of the invention, and is not intended to limit the invention to the specific embodiments illustrated.

As illustrated in FIG. 1 of the drawings, a solution container 10 includes a fluid access port 18 having a reseal assembly 20 according to the present invention for use in providing fluid communication and sealing of the solution container. The access port for a flexible fluid container constitutes one of the preferred embodiments of the present invention, although other embodiments such as a vial stopper are within the scope of the invention.

The reseal assembly 20 of the fluid access port 18 may be penetrated by a blunt entry device such as blunt cannula 12, for example to pass or withdraw fluids from the container. Blunt entry devices such as the Blunt Cannula sold by Abbott Laboratories under the registered trademark Lifeshield® are increasingly replacing the sharp needle in many medical situations.

The novel reseal assembly 20 of the present invention is used to create a fluid tight seal in a fluid access port 18, such as a port in a thin, flexible container 10. The flexible container typically is a polyvinylchloride (PVC) intravenous solution container as illustrated in FIG. 1, also referred to herein as an "I.V. bag." It is preferable to allow fluids to be passed through the reseal assembly 20, so fluids may be removed from the container 10, or be added to and mixed with the fluids in the container 10. Alternatively, the reseal assembly 20 can be used in a solution vial or in a Y-site of an infusion tubing set.

Flexible bag 10 and attachable plastic tubing 14 are of well known constructions and as such, will not be described in detail herein. Briefly, as shown in FIG. 1, the I.V. bag 10 includes two plastic sheets bonded together by a heat seal 16 along the edges of the sheets. Administration tubing 14, having an axial passage therethrough, is attached to the bag 10 by a blunt cannula 12 that is inserted through a reseal assembly 20 according to the present invention.

Figure 6:
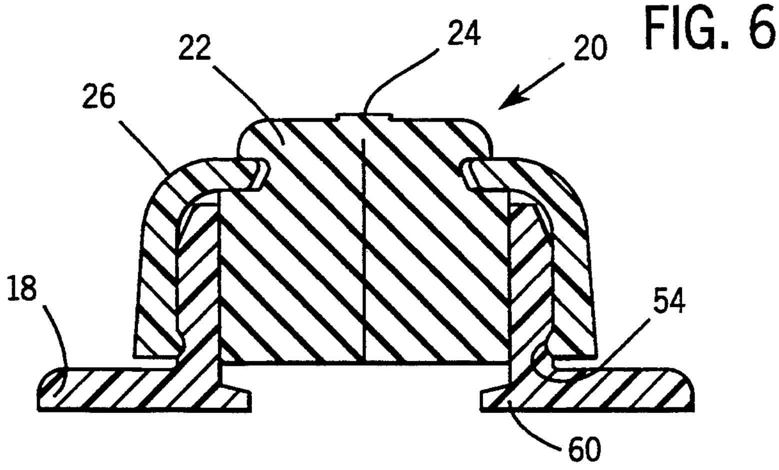
FIG. 6 is a cross sectional view of the compressed reseal assembly according to the present invention.

Referring now to FIG. 6, the reseal assembly 20 includes a resilient reseal member 22 and a reseal collar 26. The reseal assembly is provided with a target region 24 which has a reduced resistance to penetration by a blunt cannula 12, since the target area is partially pierced on the unexposed inside surface of the reseal. To administer or withdraw fluids through the reseal assembly 20, the blunt cannula 12 is passed through the reseal member 22. The reseal member 22 forms a fluid-tight seal around the blunt cannula 12. Upon withdrawal of the blunt cannula 12, the reseal member 22 reforms a fluid-tight seal and substantially prevents the passage of fluids therethrough.

The blunt cannula 12 that is used with the present invention is becoming increasingly prevalent and preferred in the healthcare industry for enhancing the efficiency with which solutions are administered to patients. The cannula 12 has a long, thin shaft 28, for example, a long thin steel shaft, having an axial passage (not shown) therethrough. The end 30 of the shaft is surface finished so as to create a blunt end. The outside diameter of the shaft 28 is small, approximately 0.050–0.070 of an inch. The smooth, blunt end 30 of the cannula 12 is highly effective in preventing a user from inadvertently being stuck with the end 30 of the cannula 12. Furthermore, the smooth end 30 prevents the blunt cannula 12 from tearing the interior of the reseal member 20 and desirably acts to prevent the cannula 12 from creating particulate when the blunt cannula 12 is passed through the reseal member 20. When the novel reseal assembly 20 of the present invention is used in combination with a blunt cannula 12, a user only needs to exert a minimal amount of force, for example, less than approximately three pounds of force, to insert the blunt cannula through the reseal member.

Referring now to FIGS. 2–6, a preferred embodiment of the port 18 and reseal assembly 20 according to the present invention is shown in greater detail.

The reseal member 22 is made of a medical grade resilient material, for example, rubber or a synthetic elastomeric material. Since the reseal member 22 is made of this material, the body of the reseal member 22 is easily displaced by the shaft 28 of the blunt cannula 12 as the cannula passes through the reseal member 22.

FIGS. 2–5 show the reseal member 22 in the uncompressed configuration as it is molded. FIG. 6 shows the reseal member 22 compressively fitted into the annular reseal collar 26. Collar 26 is then fitted to the cylindrical access port 18 which further compresses the reseal member 22.

Figure 3:
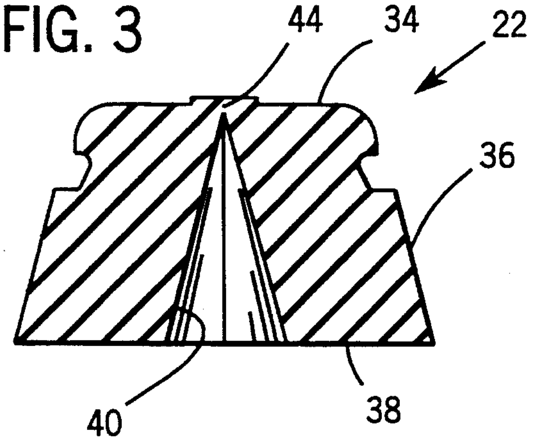
FIG. 3 is a cross sectional view along line 3—3 of FIG. 2 of the uncompressed reseal according to the present invention.

From the side view of FIG. 3, reseal member 22 has a generally frustoconical shape having a top surface 34, a circumferential side surface 36 tapering from the bottom to the top end, and a bottom surface 38.

Figure 2:
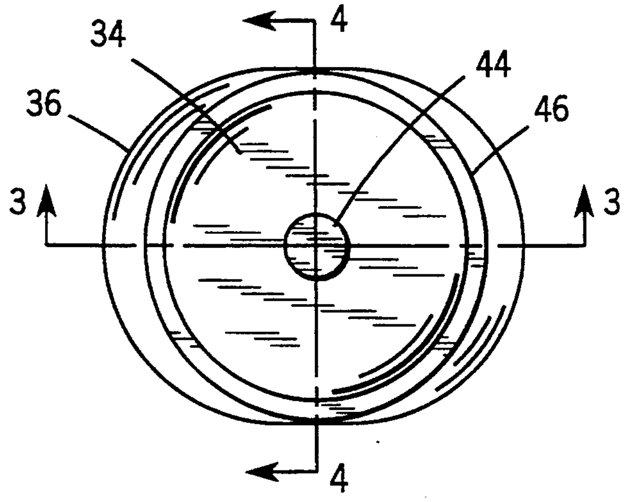
FIG. 2 is a top elevation view of the uncompressed reseal of the present invention.
Figure 5:
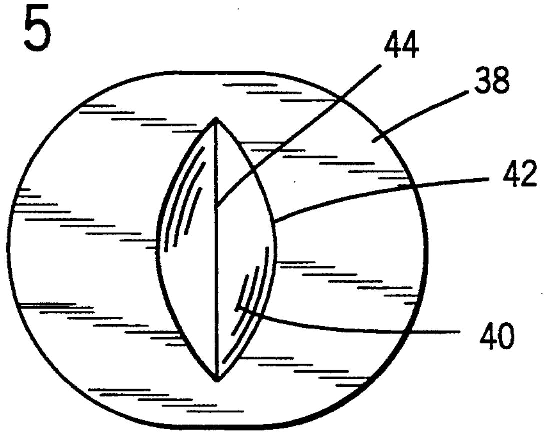
FIG. 5 is a bottom elevation view of the uncompressed reseal member of FIG. 2.

As best seen in FIG. 2, the top surface is circular. As best seen in FIGS. 2 and 5, the bottom surface 38 is eliptical, in that one axis of the bottom surface is longer than the other perpendicular axis so as to define an elipse.

Figure 4:
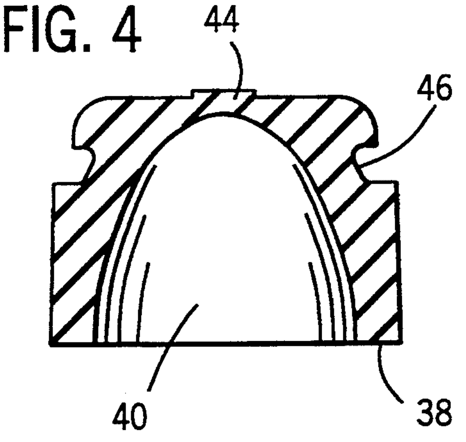
FIG. 4 is a cross sectional view along line 4—4 of FIG. 2 of the uncompressed reseal according to the present invention.

The resilient reseal member 22 also has a hollow core 40 extending from the bottom surface 38. The hollow core defines a boat-shaped opening 42 in the bottom surface 38 and has a generally rounded conical shape as seen in FIGS. 3 and 4. As best seen in FIG. 3, the hollow core tapers to a hinged region 44 just below the top surface 34 of the reseal member.

The side surface 36 has an annular groove 46 into which the inner annular edge 50 of the reseal collar is fitted.

The reseal member 22 can be molded of a resilient elastomeric material such as medical grade rubber by conventional molding processes such as compression molding. Compression molding allows the tolerances at the hinged region 44 to be better controlled than by the alternative method of cutting a slit into a rubber member. The molded configuration of the reseal member 22 can be easily reproduced within tolerance. Thus, the reseal member 22 will function within the parameters set for the reseal assembly.

Referring now to FIGS. 6, the access collar 26 is a hard but flexible plastic material such as CR3. The collar 26 can also be reproduced by known molding processes. The collar has a first radially extending inner annular edge 50 and or flange a second radially extending inner annular edge or flange 52. As previously discussed, the first inner edge 50 is fitted into the annular circumferential groove 46 molded into the outer conical surface 36 of the reseal member 22.

The second inner annular edge 52 of the collar 26 fits into a recess such as annular groove 54 on the outer surface of the access part 18. The port flexes as the reseal assembly 20 is inserted therein. The second annular inner radial flange or edge 52 further compresses the bottom portion of the reseal member 22 as the reseal assembly 20 is fitted into the cylindrical access port 18.

The fluid access port 18 is preferably made of a flexible, plastic material and includes a generally cylindrical peripheral wall with a cylindrical, axial passage therethrough. The port includes an annular shoulder 60 around the circumference of the wall at a predetermined distance from an end of the wall.

To insert the collar 26 into the passage 18, an end portion of the wall is inserted into the passage until the annular shoulder 60 generally abuts the end of the passage. Thus, the annular shoulder prevents the reseal assembly 20 from being completely inserted into the passage. The interior diameter of the passage and the exterior diameter of the access collar 26 are approximately the same size so as to create a fluid-tight fit when the collar is inserted into the passage. The collar may be attached to the passage by appropriate means.

To insert the reseal member 22 into the fluid access collar 26, the reseal member 22 is pressed into the access collar a desired distance by a suitable means. Preferably, the access collar 26 is made of a flexible, plastic material. Thus, the collar flexes as the reseal member 22 is placed therein. The interior diameter of the collar inner edge 50 and the exterior diameter of the annular groove 46 of reseal member 22 are approximately the same size so as to create a fluid-tight fit when the reseal member 22 is inserted into the collar 26.

When the blunt cannula 12 is inserted through the reseal member 22, the body of the reseal member 22 is displaced around the cannula 28 and a fluid-tight seal is formed around the cannula due to the natural resiliency of the rubber material. Thus, fluids are generally prevented from leaking through the reseal member 22. The diameter of a blunt cannula 12 is small and creates a small passage (not shown) through the reseal member 22 when the blunt cannula is inserted. After the blunt cannula 12 has been completely inserted through the reseal member 22, fluids can be passed into the container 10 or removed from the container 10, or into tubing if the reseal member 22 is provided in Y-site. When the blunt cannula 12 is withdrawn, the reseal member 22 reforms a generally fluid-tight seal due to the natural resiliency of the elastomeric material such as rubber and fluids are substantially prevented from leaking therethrough.

As best seen in FIG. 3, the reseal member 22 is molded of one integral piece and the hinged region 44 defines a preformed partial slit. The partial slit extends axially from the rearmost end of the reseal member to a predetermined position near the exposed end of the body and also across the diameter of the body. To form a partial slit, the two halves of the reseal body can be integrally formed, with a thin hinged portion 44 joining the halves, as shown in FIG. 3. The halves can then be urged together, with the portion 44 acting as a hinge. Thin portion 44 of the reseal member 22 that is forward of the slit remains as one continuous piece.

As shown in FIG. 3, the region 44 creates an area that, if penetrated by a blunt cannula 12, will allow the blunt cannula to be inserted into the reseal member 22. This is also commonly referred to as a "sweet spot." Due to the fact that the preformed slit creates this area, a user can insert the blunt cannula 12 into any point within the area. If the blunt cannula 26 is inserted into this area, the blunt cannula will pass through the preformed slit to form the passage.

One feature of note is that the reseal member 22 may include a raised ridge-like projection to provide a target 24 on the front end portion of the body. The target aids a user in inserting a blunt cannula 12 into an area that will cause the blunt cannula to be passed through the preformed slit of the reseal member 22.

While preferred embodiments have been disclosed above, it is to be understood that it is within the scope of the invention that any of the above embodiments can be easily modified for use in a side port, a down port, of a solution having a ferrule cap container or in a Y-site of an infusion tubing set. Furthermore, it is envisioned that more than one preformed slit may be used in the reseal.

From the foregoing, it will be observed that numerous modifications and variations can be effected without departing from the true spirit and scope of the novel concept of the present invention. It is to be understood that no limitation with respect to the specific embodiments is intended or should be inferred. The disclosure is intended to cover by the appended claims all such modifications as fall within the scope of the claims.

I claim:

1. A reseal assembly for penetration by an associated blunt cannula, the reseal assembly sealing a fluid port defined by a generally cylindrical wall having an open proximal end and an open distal end, the reseal assembly comprising:

a resilient body portion having a generally frustoconical shape including a top surface, a bottom surface, and a side wall surface tapering from the bottom surface to the top surface and further including a hollowed inner core opening in the bottom surface of the resilient body, the hollowed core having a generally wedge shape tapering from the open bottom surface to a hinged region near the top surface and defining two body sections positioned adjacent each other and joined to each other by at least the hinged region, said side wall surface having a groove circumferentially surrounding said body portion near the top surface; and a stiff annular collar having a first inner radially extending annular flange and a second inner radially extending annular flange, the first inner flange engaged within the circumferential groove of the resilient body so as to hold the two body sections of the resilient body in abutting contact and the second inner flange attached around the outer surface of the proximal end of the cylindrical fluid port to secure the collar and resilient body portion relative to the fluid port.

2. The reseal assembly of claim 1 wherein the resilient body is a molded material.

3. The reseal assembly of claim 2 wherein the top surface of the resilient body portion is flat.

4. The reseal assembly of claim 3 wherein the bottom surface of the resilient body portion is parallel to the top surface.

5. The reseal assembly of claim 4 wherein the hollowed core is boat-shaped at the bottom and tapers to said hinged portion of said top surface.

6. The reseal assembly of claim 5 wherein the fluid port is an access port for a flexible container.

7. The reseal assembly of claim 5 wherein the fluid port is a neck portion of a rigid vial for a medical solution.

8. The reseal assembly of claim 5 wherein the fluid port is one arm of a Y-site member for an administration tubing set.

9. An entry site for use with an associated blunt entry device, the entry site sealing a fluid port having an open bore and an attaching recess on an outside surface, the site comprising:

a resilient member having a generally uncompressed frustoconical shape including a bottom surface, a top surface, and an outside sidewall tapering from the bottom to the top;

an inner core surface extending inward from the bottom of the uncompressed resilient member and defining a generally wedge-shaped hollow core within the uncompressed resilient member, the hollow core open at the bottom of the uncompressed resilient member;

the uncompressed resilient member having two resilient body sections defined by the inner core surface and the outside sidewall, the body sections positioned opposite each other across the wedge-shaped hollow core;

a hinged region of the resilient body member between the top surface and the inner core surface and extending generally parallel to the wedge-shaped hollow core;

means for holding the resilient member in a generally compressed cylindrical shape with the two body sections in abutting contact when a resilient member is inserted into the bore of the port; and means for securing the compressed resilient member to the attaching recess of the port.

10. The entry site of claim 9 further including a circumferential groove in the outside sidewall of the resilient member and an annular collar having a first inner radially extending annular flange and a second inner radially extending annular flange;

wherein the holding means includes the engagement of the first radial flange of the collar in the circumferential groove of the resilient member and the securing means includes the mating of the second radial flange in the attached recess of the port.

* * * * *